US011395901B2

(12) United States Patent
Hsueh et al.

(10) Patent No.: US 11,395,901 B2
(45) Date of Patent: Jul. 26, 2022

(54) SYSTEMS AND METHODS FOR THERAPEUTIC GAS DELIVERY FOR PERSONAL MEDICAL CONSUMPTION HAVING SAFETY FEATURES

(71) Applicant: Philip Hsueh, El Dorado Hills, CA (US)

(72) Inventors: Philip Hsueh, El Dorado Hills, CA (US); Raymond Wu, Milpitas, CA (US)

(73) Assignee: Philip Hsueh, El Dorado Hills, CA (US)

( * ) Notice: Subject to any disclaimer, the term of this patent is extended or adjusted under 35 U.S.C. 154(b) by 676 days.

(21) Appl. No.: 16/358,961

(22) Filed: Mar. 20, 2019

(65) Prior Publication Data

US 2020/0297963 A1 Sep. 24, 2020

Related U.S. Application Data

(63) Continuation-in-part of application No. 15/714,053, filed on Sep. 25, 2017, now Pat. No. 10,525,224.

(51) Int. Cl.
*A61M 16/00* (2006.01)
*A61M 16/12* (2006.01)
(Continued)

(52) U.S. Cl.
CPC ........ *A61M 16/12* (2013.01); *A61M 16/1005* (2014.02); *C25B 1/04* (2013.01);
(Continued)

(58) Field of Classification Search
CPC .............. A61M 16/12; A61M 16/1005; A61M 2205/3306; A61M 2205/3331;
(Continued)

(56) References Cited

U.S. PATENT DOCUMENTS 3,870,616 A 3/1975 Dempsey et al.
4,747,925 A 5/1988 Hasebe et al.
(Continued)

OTHER PUBLICATIONS

The International Search Report and Written Opinion rendered by the International Searching Authority for PCT/US20/23353, dated Sep. 18, 2020, 7 pages.

*Primary Examiner* — Steven O Douglas
(74) *Attorney, Agent, or Firm* — Fresh IP PLC; Clifford D. Hyra; Aubrey Y. Chen

(57) ABSTRACT

Embodiments relate to systems and methods for gas delivery for personal medical consumption having safety features. A hydrogen or oxygen gas delivery system herein can include electrolytic cores performing electrolysis-based reactions, and obtain free hydrogen (H2) gas for collection and delivery to a user. In aspects, the electrolytic core(s) can be scaled to produce a sufficient amount of hydrogen (H2) or oxygen (O2) gas so that the user can ingest that gas directly, without a need for storage. The system can be portable, and configured with a delivery tube for transmitting hydrogen or oxygen gas to a user. While safety risks are generally minimal, the system can be configured with sensors to detect fault conditions or hazards such as combustion or overpressure, which can only be caused by deliberate user action to expose gaseous products to flame or spark, and even then would not be likely to trigger violent combustion.

19 Claims, 8 Drawing Sheets

(51) Int. Cl.
  *C25B 15/02* (2021.01)
  *C25B 15/08* (2006.01)
  *A61M 16/10* (2006.01)
  *C25B 1/04* (2021.01)
  *C25B 9/19* (2021.01)
  *C25B 9/73* (2021.01)
  *C25B 11/051* (2021.01)
  *C25B 11/057* (2021.01)
  *C25B 11/081* (2021.01)

(52) U.S. Cl.
  CPC .............. *C25B 9/19* (2021.01); *C25B 9/73* (2021.01); *C25B 11/051* (2021.01); *C25B 11/057* (2021.01); *C25B 11/081* (2021.01); *C25B 15/02* (2013.01); *C25B 15/08* (2013.01); *A61M 2205/3306* (2013.01); *A61M 2205/3331* (2013.01); *A61M 2205/3368* (2013.01); *A61M 2205/3375* (2013.01); *A61M 2205/3584* (2013.01); *A61M 2205/502* (2013.01); *A61M 2205/702* (2013.01)

(58) Field of Classification Search
  CPC .. A61M 2205/3368; A61M 2205/3375; A61M 2205/3584; A61M 2205/502; A61M 2205/702; C25B 9/73; C25B 11/057; C25B 11/081; C25B 11/051; C25B 9/19; C25B 1/04; C25B 15/02; C25B 15/08
  See application file for complete search history.

(56) References Cited

U.S. PATENT DOCUMENTS

| | | |
|---|---|---|
| 10,525,224 B2 * | 1/2020 | Hsueh .................. A61M 16/20 |
| 2011/0100328 A1 | 5/2011 | Paul |
| 2013/0112550 A1 | 5/2013 | Marsh et al. |
| 2021/0020975 A1 * | 1/2021 | Seymour .................. C25B 1/00 |
| 2021/0310134 A1 * | 10/2021 | Silva ..................... B23K 10/00 |

* cited by examiner

SYSTEMS AND METHODS FOR THERAPEUTIC GAS DELIVERY FOR PERSONAL MEDICAL CONSUMPTION HAVING SAFETY FEATURES

CROSS-REFERENCE TO RELATED APPLICATION

This application claims the benefit, including priority, of U.S. application Ser. No. 15/714,053 filed Sep. 25, 2017, entitled "Systems and Methods for Therapeutic Gas Delivery for Personal Medical Consumption", having at least one inventor in common with this application, which application is incorporated by reference in its entirety, and from which application this application, forms a continuation-in-part.

FIELD

The present teachings relate to systems and methods for therapeutic gas delivery for personal medical consumption, and more particularly, to platforms and techniques for generating, purifying, and delivering hydrogen gas for human consumption to achieve health and medical benefits and effects, the platforms and techniques being equipped with safety features to protect against potential hazards such as gas leakage or potential combustion.

BACKGROUND

In the health and medical fields, the use of treated water to produce health benefits has been known and practiced for some time. In particular, the use of ionized water as drinking water and treatment for health and medical benefits and effects has been developed and explored.

In conventional ionized water applications, drinking water can be subjected to an ionization process, in which the water can be treated to reach an alkaline state. During a conventional ionization process, water is generated near an anode which is acidic, while water generated near a cathode is alkaline. Conventional water ionizers operate by removing alkaline water near the cathode. This water will demonstrate a higher pH value (i.e. be more alkaline). In general, alkaline or ionized water can have a pH level greater than 7, for instance in the range of 7-10. Alkaline or ionized water is believed, based on various scientific and health research and investigations, to convey certain health or medical benefits to the user. The benefits may be realized or achieved for reasons including that the ionized water, which can include water infused or treated with hydrogen gas, can exhibit and present anti-oxidant properties, which help reduce free radicals in the body and offer other health benefits. Beneficial effects on digestive, metabolic, immune system, and other bodily processes have also been suggested or identified.

Known systems for the delivery of alkaline or ionized water however tend to be expensive for the average consumer. The availability of hardware to produce alkaline or ionized water can also be limited. Likewise, many or most household users may use tap water as the source of the ionized water. If that or other water source is contaminated, the quality of the ionized water may likewise be compromised. Ionized water hardware can also be bulky and hard to use for personal medical applications.

It may be desirable to provide methods and systems for gas delivery for personal medical consumption having safety features, in which other kinds of treatments for, or alterations to, water composition can be carried out to deliver hydrogen in a more convenient gaseous form, and/or hydrogen in the form of gas-infused water. According to the present teachings, the delivery of hydrogen-infused gas and/or water can produce health and medical benefits and effects for individual users using a portable, transportable, and/or otherwise convenient and effective hardware design, and providing safety measures against combustion or other unlikely but potential hazards.

DESCRIPTION OF DRAWINGS

The accompanying drawings, which are incorporated in and constitute a part of this specification, illustrate embodiments of the present teachings and together with the description, serve to explain the principles of the present teachings. In the figures.

DESCRIPTION OF EMBODIMENTS

Embodiments of the present teachings relate to systems and methods for therapeutic gas delivery for personal medical consumption having safety features. More particularly, embodiments relate to platforms and techniques for generating, separating, dehydrating and/or otherwise purifying and delivering hydrogen ($H_2$) gas and/or oxygen ($O_2$) gas to a human user to consume that substance to realize or achieve health and medical benefits and effects. According to aspects, the ingestion or consumption of hydrogen ($H_2$) gas is believed to provide a number of significant health and medical benefits and effects. One of those benefits and effects is the reduction of harmful conditions that can be caused by diabetes, including the potential reduction of A1C (glycosylated hemoglobin) levels in the blood.

Other potential beneficial effects include the reduction and/or slowing of effects due to Alzheimer's disease. Other anti-oxidant, anti-inflammatory, immune-boosting, and/or other health benefits and effects are believed to be possible from the human consumption of hydrogen gas, and/or drinking water infused with hydrogen gas. In aspects, platforms and techniques herein can likewise or instead be utilized to deliver oxygen (O2) gas to users for various purposes.

Reference will now be made in detail to exemplary embodiments of the present teachings, which are illustrated in the accompanying drawings. Where possible, the same or similar reference numbers will be used throughout the drawings to refer to the same or like parts.

Figure 1:
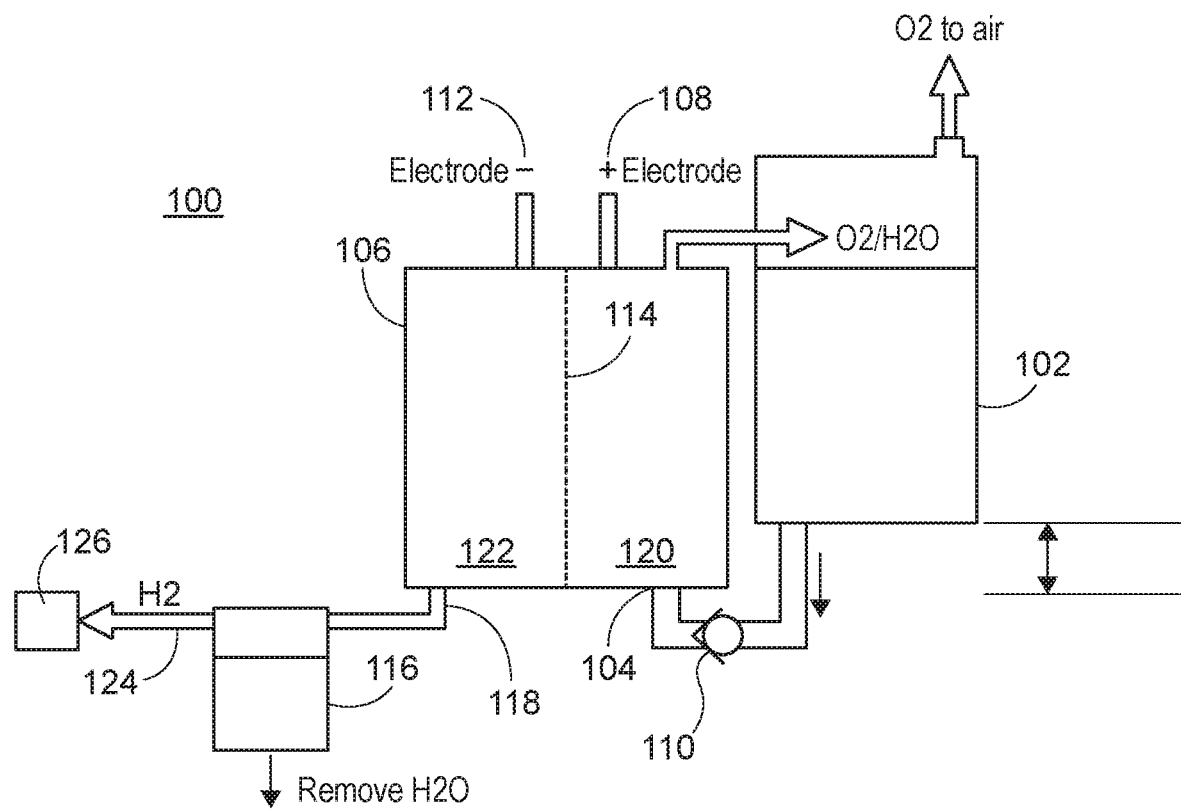
FIG. 1 illustrates an overall system which can be used in systems and methods for therapeutic gas delivery for personal medical consumption, according to various embodiments.

FIG. 1 illustrates an overall system 100 in which systems and methods for therapeutic gas delivery for personal medical consumption can operate, according to aspects. In general, the system 100 can be constructed and configured to generate hydrogen (H2) gas as an output (124), in purity and quantity sufficient to allow a human user to directly and continuously inhale the hydrogen (H2) gas and/or drink hydrogen (H2) gas-infused water, to receive health and medical benefits and effects from that consumption. According to aspects, the system 100 can be constructed and configured in an overall assembly having a size and weight to allow the system 100 to be portable, transportable, and/or easily manipulated, managed, used, and operated by the user.

In aspects, the system 100 can likewise be constructed and configured to have the capability to produce a hydrogen (H2) gas flow rate that is sufficient to deliver the gas to a human user to be consumed or ingested continuously, and/or in otherwise real-time or near real-time, which can include output rates of 50 to 250-300 ccm/minute. By scaling the generation rate of the hydrogen (H2) gas to amounts that can be consumed by a human user immediately, continuously, and/or otherwise in real-time or near real-time, any need to accumulate or store any hydrogen (H2) gas in a container for later access or use is avoided. Instead, the system 100 can be used in a personal, individual, and/or on-demand fashion at times that the user chooses.

Generally speaking, in embodiments the system 100 using hydro core 106 can produce hydrogen (H2) gas at a generation rate and/or flow rate of about 50 to 250-300 cubic centimeters of hydrogen (H2) gas per minute, which is sufficient to directly supply one user with hydrogen (H2) gas for personal, continuous, on-demand, and/or real-time or near real-time use. In embodiments, the system 100 can be constructed to produce that and/or other flow rates for a period of continuous or extended use, such as for 10 hours, during sleeping hours, and/or other periods. The hydrogen (H2) gas produced by the system 100 can be treated or purified to remove water (and/or water vapor) and/or other impurities from the hydrogen (H2) gas output 124, and can be constructed to vent or remove free oxygen (O2) gas which can build up during electrolytic or other internal reactions, thereby ensuring and managing the operational safety of the system 100. Other features and advantages of the system 100 will be described or apparent from the drawings and disclosure herein.

In aspects as shown, the system 100 can be provided or constructed with an electrolytic or hydro core 106 which can be connected to a reservoir 102. The reservoir 102 can receive, store, and distribute water to conduct electrolysis and other reactions, to ultimately generate a hydrogen (H2) gas output 124 for consumption by a user. Water received in the reservoir 102 can be manually loaded, and/or loaded using a valve or other connection or channel. In aspects, the water loaded or contained in reservoir 102 can be selected to be purified water, such as distilled, deionized, and/or otherwise treated water. In configurations as shown, the reservoir 102 can be connected to the hydro core 106 through a first port 104. The first port 104 can be or include, for instance, a pipe, tube, conduit, duct, race, funnel, orifice, and/or other channel or structure to allow fluid communication between the reservoir 102 and hydro core 106. In embodiments, the first port 104 can also include fittings such as valves, filters, gaskets, and/or other structures. In implementations, as illustrated in FIG. 1 for example. a one-way valve 110 (or check valve) can be inserted between the first port 104 and first chamber 120 or other locations to ensure a smooth flow of water and/or associated material, by for instance reducing or eliminating unintended backflow. Other flow control or other mechanisms can be used.

In general, water from the reservoir 102 can be admitted into, received in, and/or otherwise flow into the hydro core 106. In embodiments, the water from the reservoir 102 can enter the hydro core 106 via the first port 104 by draining through gravity into the hydro core 106. In embodiments, the water from the reservoir 102 can also or instead be pumped from the reservoir 102 to the hydro core 106, using a pump or other fluid drive mechanism. In embodiments as shown, the vertical clearance, or elevation between the bottom opening of the reservoir 102 leading to the first port 104 and the opening at the bottom of the hydro core 106 which receives or admits that source water, can be configured at various heights or separations, to allow the reservoir 102 to fully drain or empty into the hydro core 106 due to gravity. The water supplied from reservoir 102 can be received in the hydro core 106, which in aspects can include or contain a first chamber 120 and a second chamber 122, separated by a fluid permeable membrane 114. In general, the first chamber 120 can include an interior volume within a housing or enclosure. A positive electrode 108 can be mounted or affixed in the first chamber 120. The positive electrode can include terminals or attachments to receive an applied electric field and/or current, and can be mounted or configured to come into contact with water and fluid permeable membrane 114 through a titanium plate or other metal plate and/or meshes in the first chamber 120. In embodiments, the positive electrode 108 can be or include a platinum coated titanium electrode, but other materials and/or constructions can be used.

The hydro core 106 can include membrane 114 as noted, which can be mounted between the first chamber 120 and the second chamber 122. The membrane 114 can in general operate as a proton conductor and/or proton exchange membrane (PEM). Membrane 114 can act to allow the passage of positive hydrogen ions in one direction from the first chamber 120 to the second chamber 122, as noted herein. In general, the second chamber 122 can likewise include or enclose an interior volume within a housing or enclosure. A negative electrode 112 can be mounted in the second chamber 122. The negative electrode 112 can include terminals, contacts, or attachments to receive an applied electric field and/or current, and can be mounted or configured to come into contact with a gas diffusion layer (GDL) and fluid permeable membrane 114 through a titanium or other metal plate in the second chamber 122. In embodiments, the negative electrode 112 can be of a same, similar, and/or different construction as the positive electrode 108. In embodiments, the positive electrode 108 can also or instead be constructed in a conductive mesh configuration. When electrodes of a mesh type are used, the positive electrode 108 or similar can be constructed using two mesh elements, one with a coarse mesh construction and the other with a fine mesh construction, to increase the contact area. In aspects, the negative electric potential on the negative electrode 112 can attract hydrogen ions to the second chamber 122, where they can be collected for eventual delivery to the user.

It may be noted that while embodiments are illustrated in which the membrane 114 divides the first chamber 120 and adjacent second chamber 122 into equal and/or symmetrical volumes, in embodiments the membrane 114 can divide the first chamber 120 and second chamber 122 into different volumes. It may likewise be noted that while embodiments are illustrated in which the first chamber 120 and second chamber 122 are formed in a regular rectangular cavity, in embodiments, either or both of the first chamber 120 and second chamber 122 can be formed into other regular or irregular shapes or volumes.

In general, the hydro core 106 can operate to perform electrolysis and/or other reactions in the water in the hydro core 106 to generate hydrogen (H2) gas output 124. According to embodiments, when sufficient water has entered the hydro core 106, power control circuitry and/or software or logic can operate to apply a positive voltage to the positive electrode 108, and/or a ground potential or negative voltage to the negative e. The application of that electric potential, and/or resulting current flow between the positive electrode 108 and negative electrode 112, can cause an electrolysis reaction to take place in hydro core 106. In aspects, oxygen (O2) gas can be split from the H2O molecules of the water. In aspects, hydrogen (H2) gas can likewise be split from the H2O molecules of the water. In general, the electrolysis reaction takes place according to the following reaction:

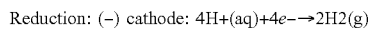

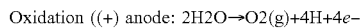 Formula 1:

As can be seen in the above expression, the electrolysis carried out in the hydro core 106 produces twice as much hydrogen (H2) gas, as oxygen (O2) gas. Each of the hydrogen (H2) gas and oxygen (O2) gas is released as bubbles into the water in the hydro core 106.

In aspects, oxygen (O2) gas can be attracted to the positive electrode 108, and drawn to migrate or collect in an area of the positive electrode 108. In aspects, the oxygen (O2) gas can be vented or released to the open air via a vent or other channels. In aspects, when current is applied between the positive electrode 108 and negative electrode 112, positive ions in the form of hydrogen (H2) gas can conversely be attracted to the negative electrode 112. The hydrogen (H2) gas can be drawn to migrate or collect in an area of the negative electrode 112, and be accumulated for eventual delivery to the user.

More particularly, in embodiments, the membrane 114 can be constructed out of a proton exchange membrane (PEM) conductive polymer film, such as a Nafion™ filter available from DuPont Co., Chestnut Run, Del. Other brands or varieties of PEM membranes or materials can be used. According to aspects, when electric current is applied to the positive electrode 108 in the first chamber 120, again hydrogen ions flow through the membrane 114 and reach the second chamber 122. Hydrogen ions may receive electrons from the negative electrode 112, and form hydrogen (H2) gas on the housing of the second chamber 122 side of the hydro core 106. The membrane 114, in embodiments, can be formed in a square filter of about 5 cm by 5 cm active area, but it will be appreciated that other sizes or shapes can be used. In embodiments, a membrane 114 of about 5 cm by 5 cm size can be capable or separating and/or generating hydrogen (H2) gas in an amount or rate of about 50 to 250-300 cubic centimeters of hydrogen gas per minute, and/or other amounts or rates.

It will be appreciated that the generation rate for hydrogen (H2) gas achieved or produced by the system 100 can be affected by a number of factors, including the volume of water contained in hydro core 106. According to aspects, the generation rate can be calculated and measured by the time of operation, and the surface area of the electrodes 108, 112 and other components in contact with the water contained in the hydro core 106 or similar. The hydrogen (H2) gas formed in the second chamber 122 can be collected to generate the hydrogen (H2) gas output 124 to be delivered for consumption by a user. In aspects, the hydrogen (H2) gas can be directed or channeled via a coalescer 116 to a second port 118 for communication to the user. The second port 118 can be of the same or a similar construction as first port 104. The coalescer 116 can be configured to remove water and/or water vapor from the hydrogen (H2). In embodiments, the coalescer 116 can be or include a hydrophobic membrane used to separate water and/or water vapor, as illustrated in FIG. 2. Hydrogen (H2) gas which arrives at the second port 118 can therefore have its water content "dried," reduced or eliminated.

Once the hydrogen (H2) gas has been subjected to the coalescer 116, the gas can be communicated to the user for consumption as the hydrogen (H2) gas output 124. The hydrogen (H2) gas output 124 can be delivered to or consumed by the user in various ways. In embodiments, the hydrogen (H2) gas output 124 can be directed to the user as a gas for direct inhalation, for instance, using medical-grade tubing and/or a breathing mask.

Figure 7:
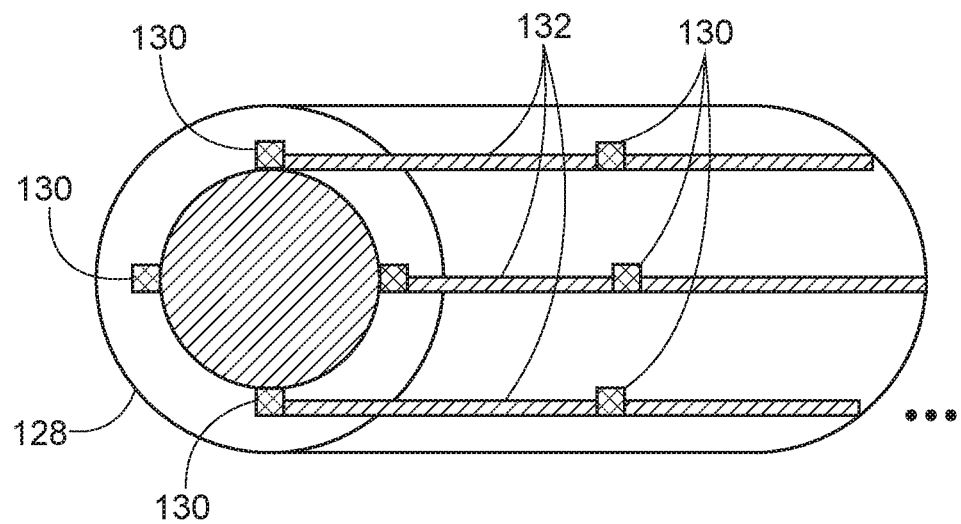
FIG. 7 illustrates an exemplary delivery tube with integrated safety features, according to various embodiments.

In aspects as shown for instance in FIG. 7, the hydrogen (H2) gas output 124 can be delivered or communicated using a delivery tube 128. In embodiments, oxygen (O2) gas can likewise or instead be delivered to a user via delivery tube 128. In embodiments, the delivery tube 128 can be attached or connected to system 100 using, for example, a snap-on or push-on fitting to attach plastic or other tube to a small flange, mount, port, or lumen for communicating gas out of system 100. In embodiments, the flange, mount, port, or lumen can be configured with electrical contacts or connectors to allow electrical communication with wiring and logic noted herein. In embodiments, the system 100 can for instance in addition or instead be fitted with fiber optic or other optical contacts or connections for signal communication. According to embodiments in various regards, it may be noted that the overall system 100 of the present teachings can be adapted or configured to deliver oxygen (O2) gas output in addition to or instead of hydrogen (H2) gas output to the user, since both types of gas are natural products of the system and processes according to the present teachings.

In either case or on other rare occasions, it may be noted that a possibility could exist for the combustion of the output gas, even though the overall system 100 is not likely to be prone or vulnerable to accidental combustion or other accidents. This is due to more than one safety factor built into system 100, including that at the overall amounts or flow rates of hydrogen (H2) gas generated, it will be difficult or impossible to initiate some type of combustion. At generation and flow rates as noted, the hydrogen (H2) and/or oxygen (O2) gas will tend to evaporate or disappear even if a gas leak develops. Moreover, a user would almost have to deliberately apply heat or flame to even potentially initiate combustion of those gaseous products, and even in that highly unusual circumstance, the gaseous products would most likely merely burn in a blue flame, rather than violently or spontaneously combust. Those limiting factors and operational safety margins apply at or around other areas of system 100, in addition to the actual delivery tube 128.

Nevertheless, configurations according to the present teachings are intended to include safety features and fault detection to create maximum margins of safety, for example in instances where the gas is accidentally exposed to heat, flame such as from a cigarette or candle or other source, spark, or other conceivable hazards in the general environment of system 100.

According to embodiments, therefore, and as shown for instance in FIG. 7, according to aspects herein in applications it may be useful to equip the delivery tube 128 and/or other components with a set of sensors 130 to attempt to detect, prevent, and/or respond to hazardous conditions or events. According to aspects, the set of sensors 130 can be or include electric or electronic parts connected by circuits 132, such as electrical wiring that may be embedded in the delivery tube 128, for instance, by embedding the circuits 132 in thermoplastic, resin, or other material used to fashion delivery tube 128 when the tube is formed. In embodiments as shown, the circuits 132 can be configured in a lengthwise arrangement, but it will be appreciated that other physical construction, such as concentric spiral wiring, can be used. Circuits 132 can in addition or instead for instance be affixed to an interior surface of delivery tube 128 after that tube is made, for example, by gluing or otherwise adhering the circuits 132 to the interior wall of delivery tube 128. The set of sensors 130 can in applications be or include, for instance, electrical sensors such as resistance sensors or thermistors, pressure sensors, acoustic sensors, chemical sensors, optical sensors, and/or other types of sensors. It may be noted that in embodiments, the delivery tube 128 can be configured with multiple identical or other sensors along the length of delivery tube 128 so that cuts or other damage at different points of delivery tube 128 can be detected, identified and/or localized. When so equipped, the set of sensors 130 can be spaced at equal or unequal intervals. Other construction techniques or configurations of the delivery tube 128, circuits 132, as well as the set of sensors 130 and other components are possible.

In operation, the power control unit 310 or other programming or logic can monitor various conditions or parameters in delivery tube 128 and/or other parts of system 100 to detect and/or prevent dangerous conditions or events that could conceivably take place during use of system 100. For example, one hazard that could conceivably be present is the possibility of combustion taking place through exposure of a combined hydrogen (H2) gas/oxygen (O2) gas mixture to a spark or flame, although this again is unlikely without a user deliberately exposing the gaseous products to a spark or flame. Even in that unlikely event, the most likely result would be some type of blue-flame or other limited burning. In aspects, the set of sensors 130 can be or include temperature sensors that can detect, for instance, temperature reaching a predetermined limit or threshold in the delivery tube 128. In applications, the power control unit 310 and/or other programming or logic can be configured to monitor electrical continuity in the set of sensors 130 and/or circuits 132, to detect situations such as where the delivery tube 128 is broken, kinked, or severed, for example due to potential combustion, accidental breaks or cuts, and/or other events. In Implementations, the set of sensors 130 can likewise be configured to be or include one or more pressure sensors, for instance to detect an acoustic wave, overpressure or underpressure state in the delivery tube 128. An overpressure or underpressure or other fault condition might exist, for example, when delivery tube 128 becomes blocked, bent, folded, stretched, cut, bulged, and/or otherwise obstructed or damaged. Detection of fault conditions of various kinds can be used to cut off power to system 100 or parts of the system.

Upon detection of any one or more of these or other fault conditions, the power control unit 310 and/or other programming or logic can as noted initiate or undertake various actions in response. For example, the power control unit 310 and/or other programming or logic can cut off electrical power to the system 100 entirely, to prevent further damage to the system 100 and protect the safety of the user. Other actions can be taken. In aspects, the power control unit 310 and/or other programming or logic can capture information related to the detected fault condition to report that information to a networked monitoring service or system, for instance, a cloud-based or other service or system.

When delivered in gaseous form, the user can affix the delivery tubing, 128, any attached mask, cannula, and/or other breathing apparatus for use at desired times. In aspects, a user can apply a breathing mask during sleeping hours, for convenient consumption of the hydrogen (H2) gas output 124 during overnight or other periods. In embodiments, the delivery rate of the hydrogen (H2) gas and/or oxygen (O2) gas output can be adjustable for periods of sleep. Other delivery techniques, such as tubing which is attached or mounted close to the user's nose, can also be used.

Figure 8:
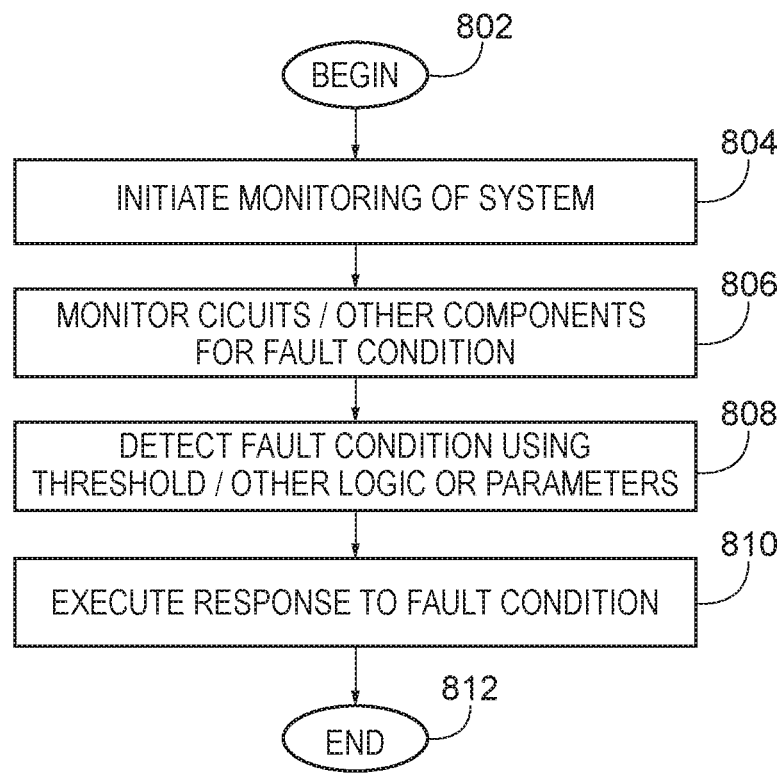
FIG. 8 illustrates an exemplary flow diagram of safety operation, according to various embodiments.

An exemplary flow diagram of safety and related processing is illustrated in FIG. 8, according to various further regards. In 802, processing can begin. In 804, the power control unit 310 and/or other control logic can be initiated, for instance, to verify the presence or integrity of circuits 132, the set of sensors 130, and/or other hardware or operation of system 100. In 806, the power control unit 310 and/or other control logic can monitor the circuits 132, set of sensors 130, and/or other components or operational parameters of system 100 to detect one or more potential fault conditions, such as sudden or other changes in resistance values, temperature, pressure, and/or other operational details associated with system 100.

In 808, a fault condition in system 100 including delivery tube 128 can be detected, for instance by comparing resistance, temperature, electrical current, and/or other parameters to predetermined safety values or thresholds, and/or otherwise detecting those or other signals or conditions, such as pressure or acoustic wave signals.

In 810, the power control unit 310 and/or other control logic can initiate or execute a response to the fault condition, such as to execute protective or corrective action. For instance, the power control unit 310 and/or other control logic can cut off electrical power to system 100 or individual components of system 100, eliminate or reduce the generation of oxygen or hydrogen gas, and/or other actions. In 812, processing can repeat, jump to a further processing point, return to a prior processing point, or end. For example, in cases or relatively minor or unverified fault conditions, the power control unit 310 and/or other control logic can reset to a non-fault state, or take other action.

In embodiments, the hydrogen (H2) gas output 124 can also or instead be delivered to the user by injecting the hydrogen (H2) gas output 124 into drinking water, to dissolve the hydrogen (H2) gas into the water, which is then ingested by the user. When delivered in water, the hydrogen (H2) gas output 124 can be directed into a container using a nozzle or other structure to introduce the hydrogen (H2) gas output 124 into the water, where the hydrogen (H2) gas output 124 is dissolved. In embodiments, an optional micro porous element 126 can be provided before delivery to the drinking water, which forces the hydrogen (H2) gas into small bubbles to increase contact surface area with the water.

A micro size (in microns) for the micro porous element 126 can help to dissolve the hydrogen (H2) gas into the water. It may be noted that the saturation point for hydrogen (H2) gas in water is about 1.6 milligrams per liter at room temperature, which reflects a fraction of generated hydrogen (H2) gas entering the water, while the rest escapes into the surrounding air. If desired, the user can inhale the evaporated hydrogen (H2) gas from the water, to maximize the intake or usage of the hydrogen (H2) gas.

One way to test or characterize treated hydrogen (H2) gas-enriched water for human consumption is to detect or measure the oxidation reduction potential (ORP) of the water. In embodiments, the IOT control unit 312 and/or other logic can be configured to measure the ORP by detecting voltage potential in the water. Ordinary or tap water can typically be measured at a positive ORP level, for example 100 millivolts to 300 millivolts (positive potential), although values can vary in different locations or conditions. It is generally believed that treated water must develop an ORP of at least −250 (negative) millivolts to produce health benefits. According to aspects, it will take about 1 to 2 minutes to reach an ORP level of −250 to −500 (negative) millivolts, when injecting about 200-300 cubic centimeters per minute of hydrogen (H2) gas into a half liter of water.

In embodiments, the additional or residual water can be returned to the reservoir 102, to provide more water to the reservoir 102 to feed the overall electrolysis reaction. According to embodiments, when the reservoir 102 is loaded with water, such as purified water, normally the force of gravity is enough to drain the water down in the reservoir 102, through the first port 104 and into the hydro core 106.

Figure 2A:
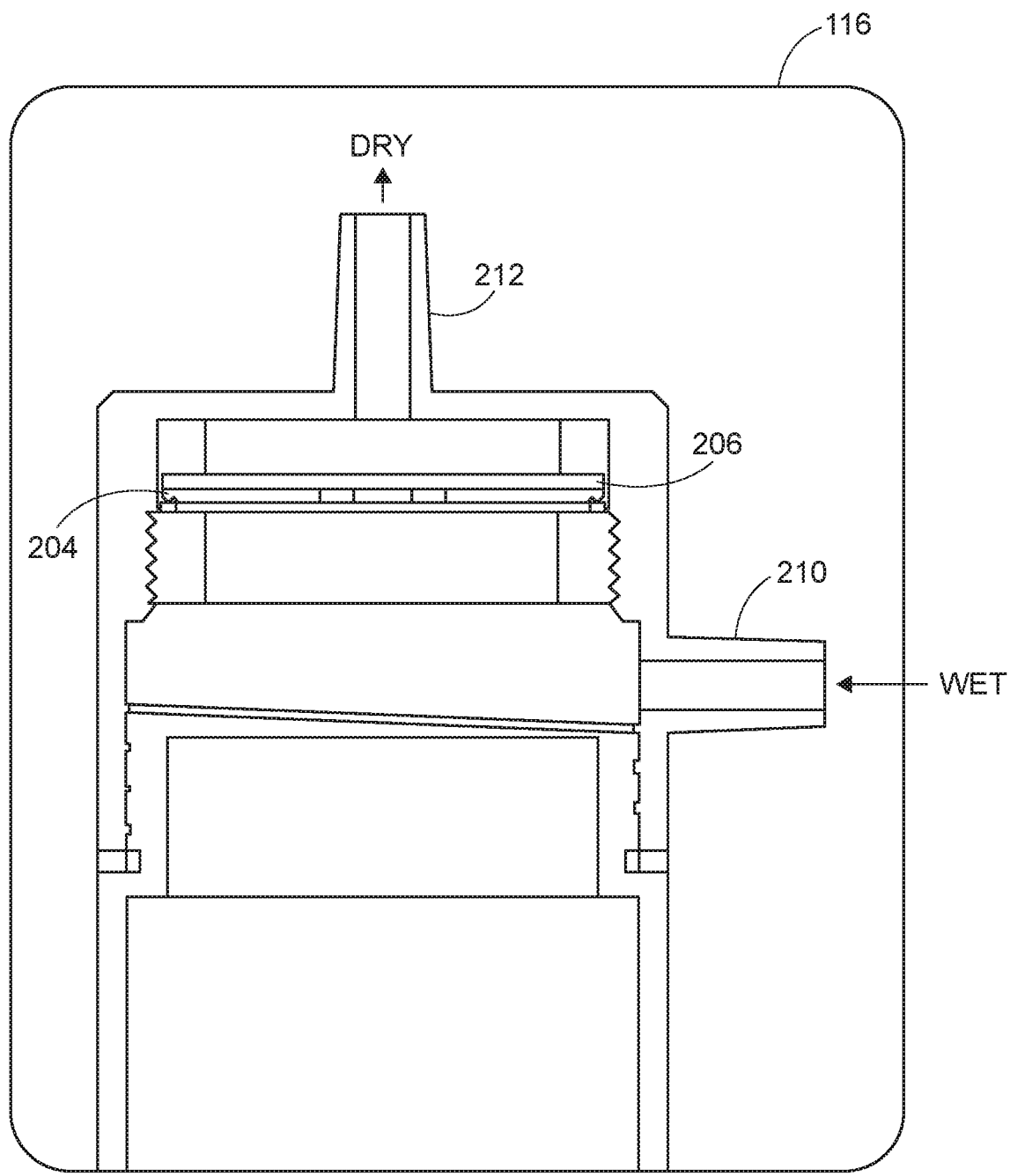
FIGS. 2A and 2B illustrate an example of a construction of a coalescer unit that can be used to treat output hydrogen gas delivered by systems herein, according to various embodiments.
Figure 2B:
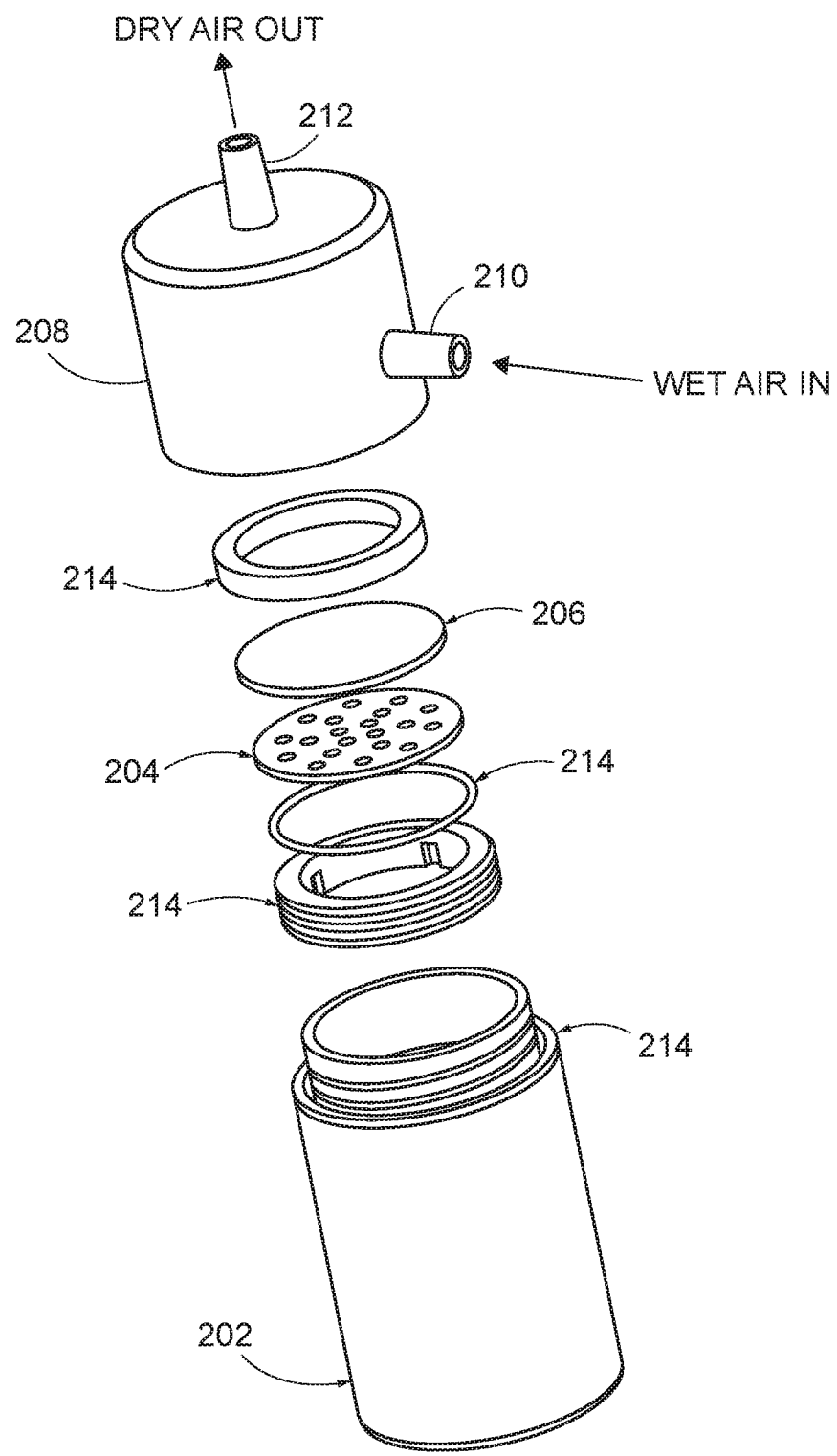

In embodiments, as noted, the overall system 100 can include a coalescer to dry the hydrogen gas (H2) output. FIGS. 2A and 2B show an illustrative construction for coalescer 116 and similar units that can be used to remove water and/or water vapor from the hydrogen (H2) gas output 124 generated for consumption by the user. As shown in FIG. 2A, coalescer 116 can include an inlet port 210 into which untreated, moist, or wet hydrogen (H2) gas can enter after generation in the hydro core 106 or similar. The coalescer 116 can be constructed in a screw-down, canister form. Located in the coalescer 116 above the inlet port can be structures including a condenser 204 and a hydrophilic membrane 206, which can be 13 mm, 25 mm diameter, and/or other diameter or sizes. The hydrogen (H2) gas can enter the coalescer 116 and water and/or water vapor contained in the hydrogen (H2) gas can be trapped, repelled, or otherwise guided downwards into canister 202, due to the water repellent properties of the hydrophobic membrane 206. Water and/or water vapor can collect into canister 202 as hydrogen (H2) gas flows to the user via outlet port 212.

As shown in FIG. 2B, the hydrogen (H2) gas can be communicated to a separator housing 208 and exit through outlet port 212 as a "dry" gas. After that conditioning, the water and/or water vapor reduced or eliminated from the hydrogen (H2) gas before use or consumption by the user.

As also shown for example in FIG. 2B, the separator housing 208, canister 202 and other elements of the coalescer 116 can be attached or secured using a set of fittings 214, such as spacers, O-rings, and nuts, as illustrated. It will be appreciated however that other fittings, attachments, and overall constructions for coalescer 116 can be used. In embodiments, the water collected in canister 202 can be collected for draining, disposal or recycled back to reservoir 102. In embodiments, the coalesced water can be removed manually, and/or electronically using a valve 328 or other fluid control controlled by power control unit 310, IOT controller 312 (shown in FIG. 3), or other logic or control.

Figure 3:
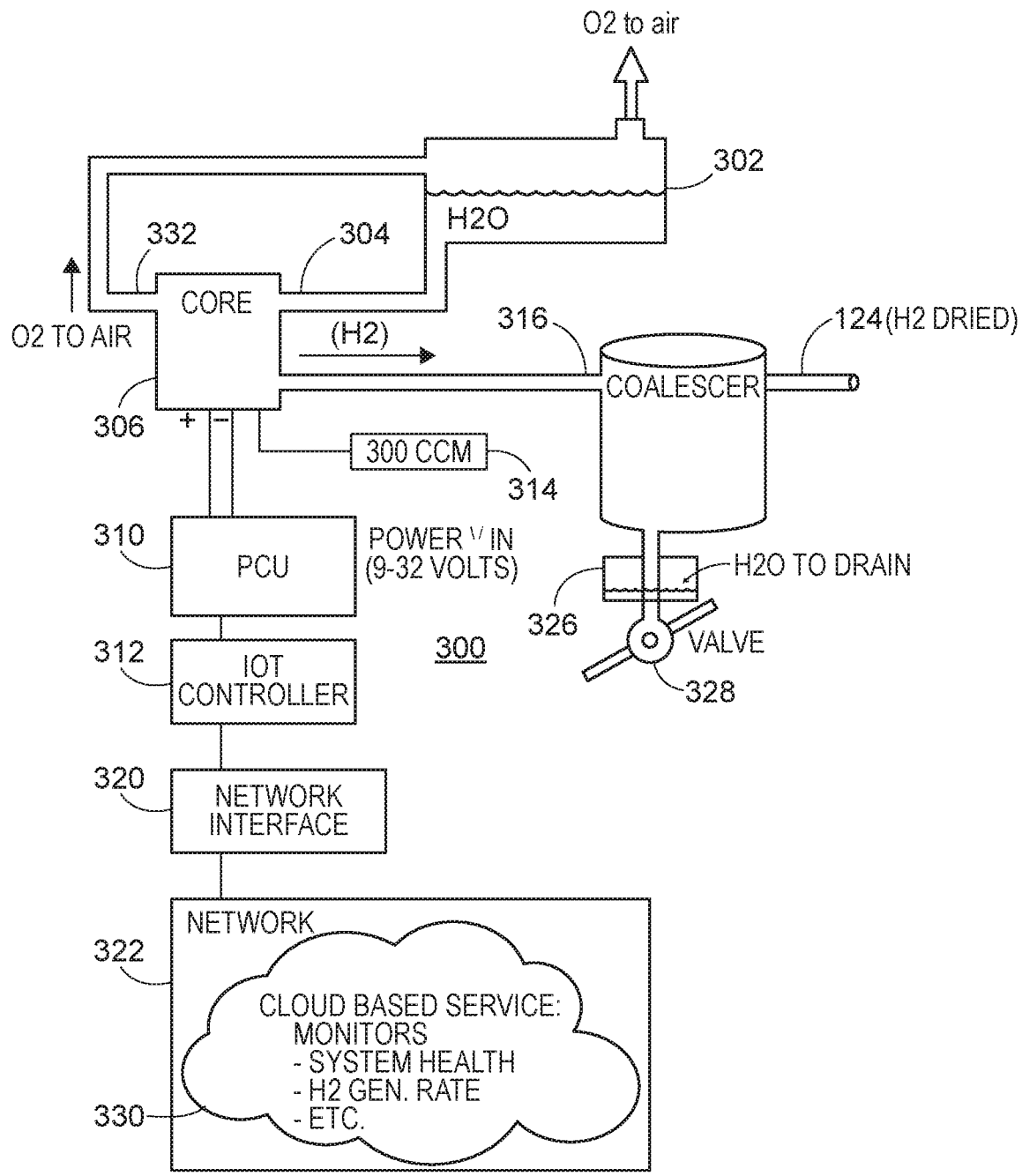
FIG. 3 illustrates an overall system which can be used in systems and methods for therapeutic gas delivery for personal medical consumption, according to various embodiments in further regards, including various aspects of logic control.

An overall system 300 according to aspects of the present teachings is shown in FIG. 3. The system 300 of FIG. 3 can be constructed generally in the same or similar configuration shown in FIG. 1, while also illustrating control logic and other features that can be incorporated into system 300, according to embodiments. FIG. 3 depicts a system 300 generally in terms of a block diagram, including modules, hardware, and/or logic for the control of hydrogen (H2) gas 42 generation operations. In aspects as shown, a reservoir 302 can be fluidly connected to at least one hydro core 306, via a first port 304, such as for instance a pipe, channel, and/or other conduit. On the output side of the electrolytic core 306, hydrogen (H2) gas output 124 along with water or water vapor can be communicated via a second port or other channel to a coalescer 316. The coalescer 316 can be of the same or similar construction as coalescer 116 shown in FIG. 1, and can produce a "dried" output of hydrogen (H2) gas 42 for consumption by a user. In aspects, the generation rate for the hydrogen (H2) gas can be in the range of about 250-300 cubic centimeters per minute using one hydro core 306, but other ranges or rates can be produced. In aspects as shown the coalescer 316 can divert or tap off water and/or water vapor to a container 326 or other container to drain or otherwise process.

In terms of operation and control of the system 300, in embodiments as shown the hydro core 306 can be electrically connected to a power control unit 310. The power control unit 310 can be a programmed processor or other logic equipped or configured to manage the delivery of electrical power to the hydro core 306, including to positive and negative electrodes (not shown) arranged in the hydro core 306, which can include electrodes which are the same or similar to the positive electrode 108 and negative electrode 112 shown in FIG. 1. In aspects, the power control unit 310 can receive an input voltage in the range of 9 to 32V, and deliver current to or across the hydro core 306, for example in a range up to 40 amperes (direct current). Power consumption of for example about peak 120 watts can be demonstrated, but while certain ranges for voltage, current, and wattage are noted, it will again be appreciated that other ranges or values, or combinations of ranges or values, can be used.

In embodiments, the power control unit 310 can be configured to maintain a constant voltage and/or a constant current supply to the electrolytic core 306, although variable voltage and/or current can be used in embodiments, as desired. In embodiments, the power control unit 310 can be configured to receive direct current (DC) converted from a standard alternating current wall outlet, for instance, by using an inline AC-to-DC conversion transformer (not shown) built into a power supply cord. In embodiments, the power control unit 310 can also or instead be configured to operate using a direct DC power source, such as an external battery, internal battery, or other battery or source. In embodiments, the system 300 can be configured to operate off of a standard automobile battery producing 12 or 24 volts. In embodiments, if a battery is used, a battery unit can in aspects be integrated into system 300 and/or be provided as an external unit to the system 300. In embodiments, a battery power source can be used if it is desired to make the system 300 portable and/or easily transportable. It will be appreciated however that the system 300 can be made to be portable and/or easily transportable using a variety of other power sources or types (AC or DC), as well. In embodiments, if a battery is used as a power source, the battery can be or include one or more types of batteries or cells, such as lead acid, and/or other varieties or types of stored energy batteries or cells.

According to aspects as likewise shown, in embodiments an Internet of Things (IOT) control unit 312 can be provided in electrical and/or logical communication with the power control unit 310 and/or other components or resources of system 300. In aspects, the IOT control unit 312 can be equipped with hardware and/or software resources to carry out logic control over system 300. The IOT control unit 312 can for instance include one or more processors, electronic memory, hard disk or other storage, and a network interface 320, among other resources. The network interface 320 can be or include a wired connection, such as an Ethernet connection, and/or a wireless connection, such as a Bluetooth or Wi-Fi air interface.

The network interface 320 can communicate with a network 322, such as the Internet, a cloud-based network or service, and/or other public or private network, channels, or connections. In embodiments, the network 322 can be or include the Internet of things (IoT), and/or other networks or services.

In aspects, data related to the delivery and/or use of consumption of hydrogen (H2) gas can be stored in the system 300 and/or uploaded or stored to a monitoring service 330 hosted in network 322, for instance to create a user history or profile which monitors the overall health and operation of system 300, including parameters such as run time, generation rate, system temperature, fault events, and/or other operational variables. [0052]. The user history or profile can, in embodiments, likewise include other medical data related to the user and be stored or communicated to in monitoring service 330, to assist in better evaluating the user's health or medical state over time, as well as operation of system 300. The additional medical information can include information such as, but not limited to, pulse rate, blood pressure, body temperature, and/or other vital signs, readings, or information, as desired. In embodiments, that or other medical information can be collected using additional or accessory instruments, or devices configured to operate with system 300, such as blood pressure monitors or pulse oximeters provided with a BlueTooth™, WifFi, or other network interface. In embodiments, those or similar measuring devices can be integrated in system 300 itself. In aspects, the system 300 can therefore serve as a gateway to capture or transmit personal medical information, for instance, to a cloud-based or other monitoring service, and/or other destination. In embodiments, the capture or transmission of vital signs and/or other information can be carried out by system 300 during hydrogen (H2) gas generation operations, or can be carried out at other times, including during which system 300 is not carrying out hydrogen (H2) gas generation operations.

In aspects, the system 300 can likewise be set up to receive data and/or configuration instructions from the network 322, such as for instance to periodically update any firmware, software, or other software resources contained in or associated with the system 300. In embodiments, other information or data can be captured by or through system 300 and related services, such as video of a patient in a facility, motion detection data, and/or others The IOT control unit 312 can in aspects be configured to monitor and/or control the operation of the power control unit 310, set of sensors 130, and/or other elements, controls, or devices contained in or used by the system 300. According to embodiments, the IOT control unit 312 can be connected to an integrated display 314, such as a light emitting diode (LED), liquid crystal display (LCD), and/or other display or monitor. In aspects, the display 314 can be configured to display various data and variables related to the operation of the system 300, including a numerical display of the generation rate of the hydrogen (H2) gas being produced and output for consumption by the user. In embodiments, the cloud-based monitoring service can be configured to transmit system or medical data to a networked device to display, such as a smart phone operating a compatible application, or otherwise.

The generation rate can be refreshed at intervals, such as every 15 seconds, minute, or other intervals. In embodiments, the generation rate can be expressed in terms of cubic centimeters of hydrogen (H2) gas being delivered to the user, but other units can be used. While various control operations have been described as being performed by the power control unit 310 and/or IOT control unit 312, it will be appreciated that in embodiments, the same or other control operations can be carried out by the power control unit 310 by itself, by the IOT control unit 312 by itself, by different combinations of operations performed or shared by the power control unit 310 and IOT control unit 312, and/or by other circuits, modules, or logic.

In aspects, the IOT control unit 312 can also control or manage other operations or parameters related to system 300, and generate and/or display other information or data. For instance, in embodiments, the IOT control unit 312 and/or monitoring service 330 can be configured to generate an alert to the user when the hydrogen (H2) gas generation rate and/or other parameters go out of range, and/or otherwise become abnormal or reach a fault or error state, vital sign being monitored reach a significant level, and/or other conditions are met. In aspects, an alert can be provided, for instance, by lighting up a red light or icon on the display 314, and/or a user interface on an application tied to the monitoring service 330, and/or other interface. In embodiments, the IOT control unit 312 can cause text to be displayed on the display 314, such as "error," "warning," and/or other words or messages. In embodiments, the IOT control unit 312 and/or monitoring service 330 can also or instead generate an audible alert or warning, such as a beeping sound, computer-generated speech, and/or other audible annunciations or alerts. The IOT control unit 312 can also, in embodiments, be configured to transmit or communicate status information, including alerts or notifications, to additional remote stations, services, and/or data stores via network connection 320 and network 321.

According to embodiments, the IOT control unit 312 and/or other logic can also calculate, estimate, and/or monitor the rate of hydrogen (H2) gas generation, for instance using electrical parameters or other variables of the system 300. In aspects, the hydrogen (H2) gas generation rate can be calculated or estimated, at a known, estimated, or measured temperature, using the amount of electrical current applied to the hydro core 306. In general, the hydrogen (H2) gas generation rate can be modelled as proportionate to the amount of applied voltage and/or current. In addition, the volume of needed water to conduct electrolytic operations and generate a desired hydrogen (H2) gas generation rate can be calculated or estimated.

According to embodiments in further regards, if the IOT control unit 312 or other logic detects decreasing or zero electrode current levels, the IOT control unit 312 can be configured to identify low hydrogen (H2) gas flow rates, and/or a low supplied water level to the system 300. Under such conditions, the IOT control unit 312 can again generate an alarm or notification, such as a flashing light, text or audible warning, and/or transmit a fault status message to network 322, monitoring service 330, and/or other node, service, or destination.

According to aspects in yet further regards, the IOT control unit 312 can be configured with timing circuitry or logic, such as a chip designed for use as a timer or clock, to program the system 300 to operate at certain times or intervals. In embodiments, IOT control unit 312 can be configured to allow the user to program or set desired times or intervals for operations, and/or to provide other settings for the use or operation of the system 300.

As noted, in embodiments the generation rate can be in the range of about an adjustable range of 50 to 250-300 cubic centimeters of hydrogen (H2) gas per minute using a single electrolytic core, which can be adjustable or programmable, but it will be appreciated that that range is merely illustrative, and different lower and upper values can be used or achieved. The output hydrogen (H2) gas can once more be delivered or communicated via an outlet port, tube, mask, dissolver or other mechanism for consumption as a gas, or introduced into water for drinking or ingestion.

While foregoing embodiments, including those illustratively shown in FIG. 1 and otherwise, depict embodiments in which a single hydro core 106 is used to conduct electrolytic reactions and produce hydrogen (H2) gas, in embodiments two or more electrolytic cores can be combined or joined to increase the generation rate, and/or other properties or capabilities of the system.

According to embodiments a set of multiple hydro cores 106 or similar can be combined, ganged, or "stacked" to increase the generation rate of hydrogen (H2) gas in one unit. In aspects, the generation rate for such a unit can be scaled or increased compared to a single hydro core 106 with similar capacity. The number of cores can accordingly, in aspects, be chosen to reach or produce a desired generation rate of the hydrogen (H2) gas which can be delivered to the user. In general, as noted, a system using one electrolytic core according to embodiments herein can generally produce a hydrogen (H2) gas flow rate of about 50 to 250-300 cubic centimeters per minute, and/or other flow rates or ranges. According to embodiments, however, if desired, a system using two electrolytic cores 106 in the set of cores can generally produce hydrogen (H2) gas flow rate of about 500 to 600 cubic centimeters per minute, and/or other flow rates or ranges.

The electrical control provided by the power control unit 310 or similar, control or monitoring provided by the IOT control unit 312, or similar, and/or other logic or control can be adapted to service multiple cores, such as to ensure desired voltage or current values are maintained in each of the subject cores. When two or more cores are used, the outlet port can be configured to form a channel through which continuous fluid communication is maintained, to allow all hydrogen (H2) gas generated in the set of cores to be collected and delivered to the user as one stream. It will be appreciated, as well, that while the several cores can be of the same or similar configuration, including size or dimension, in embodiments the first, second, and/or other numbers of cores can be fabricated with the same or with different configurations, including size or dimension.

Figure 4:
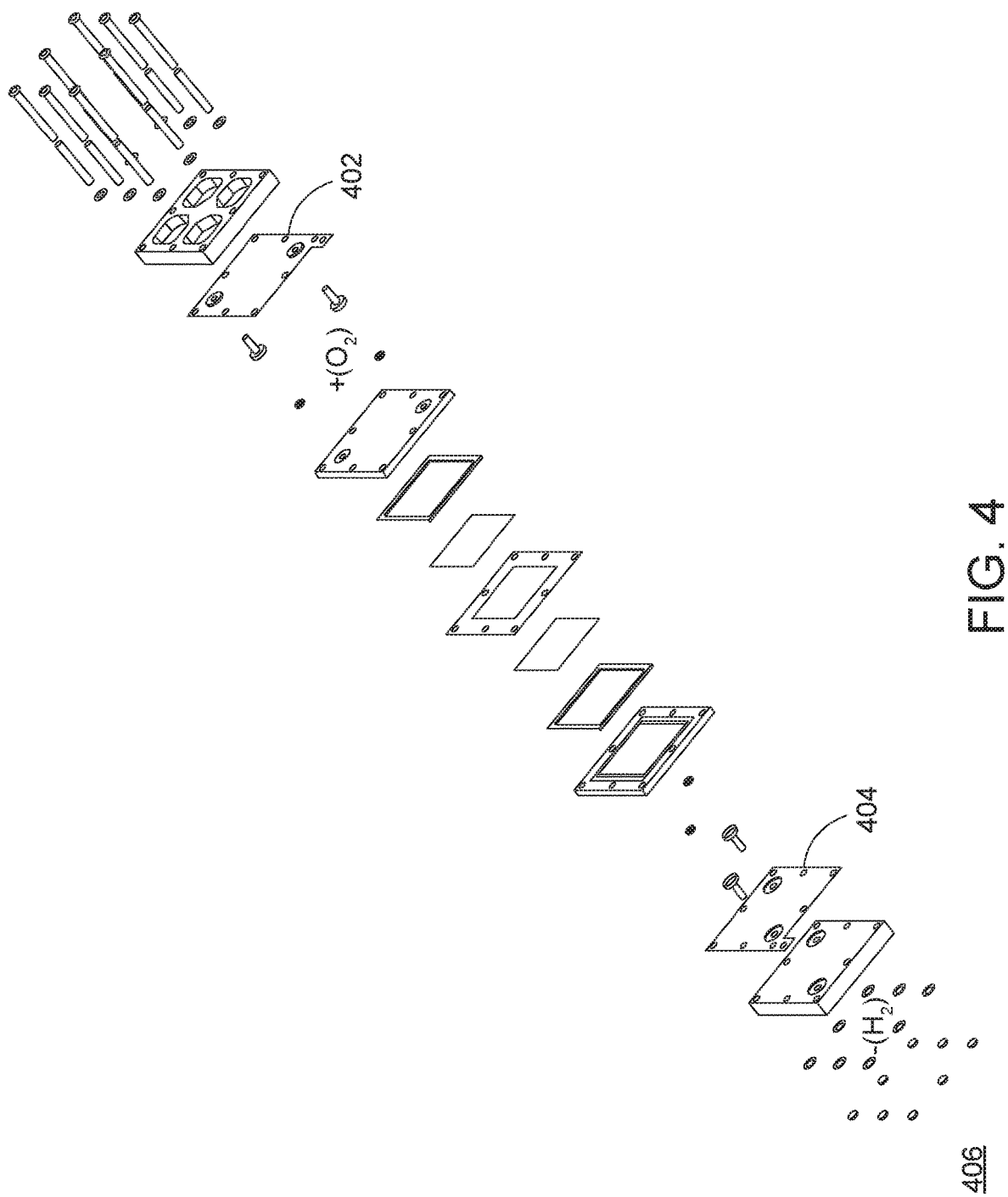
FIG. 4 illustrates various details of a construction of a hydro core that can be used according to various embodiments.

Various aspects of an illustrative construction of the hydro core 106 are shown in FIG. 4. According to aspects shown in FIG. 4, internal configurations of hydro core 106 can be used in which a positive connection for a voltage potential is configured using a positive terminal 402 to provide a potential for electrolytic reactions. Conversely, a negative terminal 404 can be provided using a cathode (negative) electric plate, generally opposed to the positive terminal 402 in an opposed planar orientation. In general, the voltage potential between the positive terminal 402 and negative terminal and resulting current flow can be used to drive electrolytic and/or other reactions in hydro core 106.

In aspects as shown, the positive terminal 402 and negative terminal 404 can be secured, opposed, mounted, and/or connected using fittings such as screws, bolts, nuts, and O-rings, as shown. It will be appreciated however that other fasteners, connectors, or techniques can be used to assemble and connect components of the hydro core 106, and/or other components or structures of system 100 (300) or similar, and/or that hydro core 106 can be stacked or ganged, a noted herein.

Figure 5:
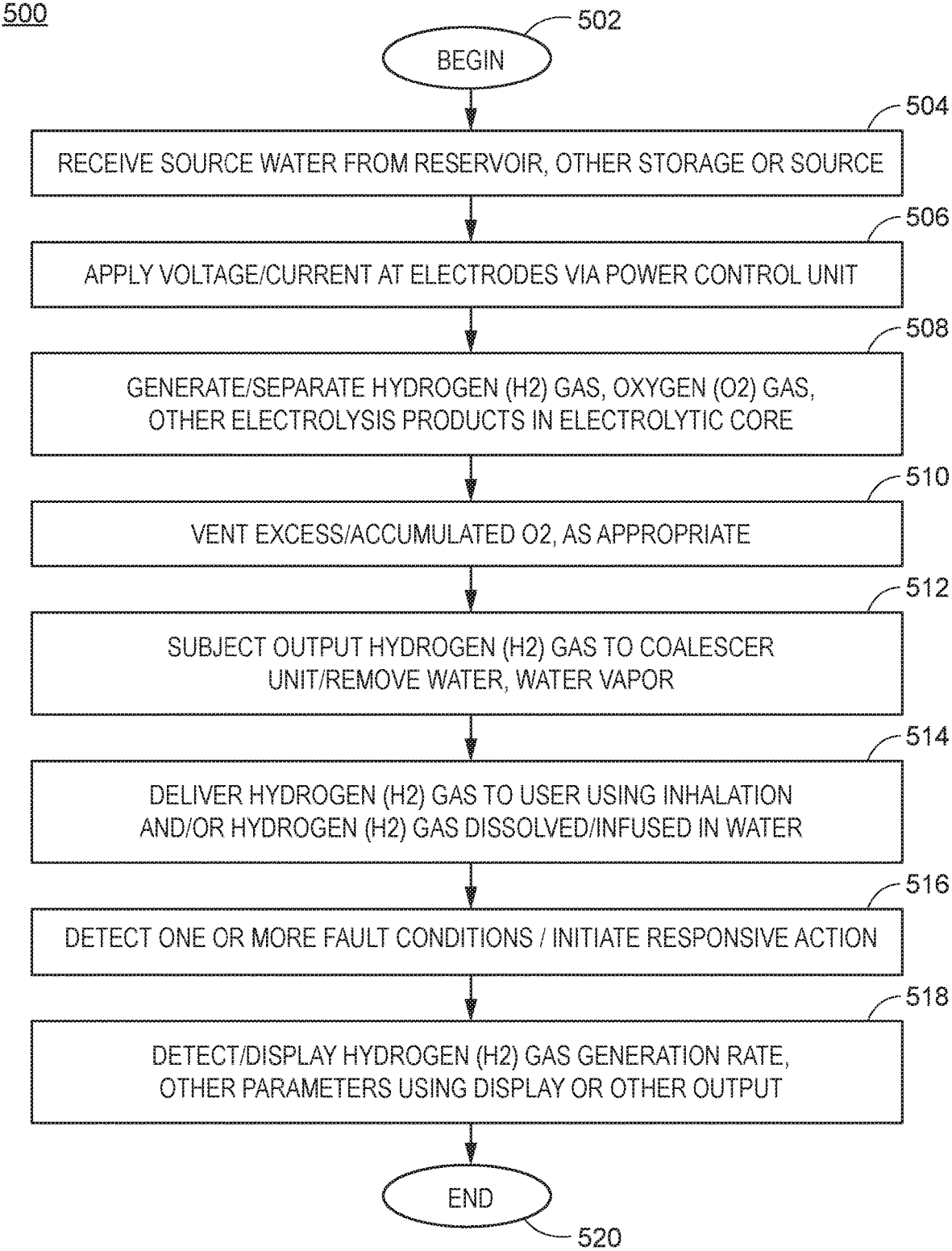
FIG. 5 illustrates a flowchart of various processing that can be used in hydrogen gas delivery for personal medical consumption, according to various embodiments.

FIG. 5 illustrates a flowchart 500 of power control, monitoring, gas generation, and other processing that can be performed in systems and methods for therapeutic gas delivery for personal medical consumption, according to aspects in various regards. In 502, processing can begin. In 504, a supply of water can be received in the hydro core 106 from reservoir 102 via first port 104. In embodiments, the water received from the reservoir 102 can be distilled, deionized, or otherwise treated 'purified water. In embodiments, as noted the first port 104 can be or include a pipe, conduit, duct, funnel, and/or other channel or fluid connection between the reservoir 102 and the hydro core 106. In embodiments, the water can be introduced to the hydro core 106 from the reservoir 102 under force of gravity, and draining directly into the hydro core 106. In embodiments, the water can be transmitted from the reservoir 102 to the hydro core 106 using a pump and/or other fluid driver.

In 506, in hydro core 106 a voltage can be applied to the positive electrode 108 and negative electrode 112 or similar electrodes or contacts using a power control unit, and/or other controller or logic. In embodiments, the voltage across the positive electrode 108 and negative electrode 112 can be established or maintained at desired or predetermined levels or ranges, such as 1-3 volts, or other levels. In embodiments, the current between the positive electrode 108 and negative electrode 112 can also be established or maintained at desired or predetermined levels or ranges, such as up to 40 amps. Other values can be used.

In 508, the oxygen gas (O2) and hydrogen gas (H2) products of an electrolysis reaction in the hydro core 106 can be separated in the hydro core 106. In aspects, the positive electrode 108 can attract oxygen products, while the negative electrode 112 can attract hydrogen products. The membrane 114 can act to prevent oxygen (O2) and other products from traveling to the second or negative electrode side of the hydro core 106, while allowing the hydrogen (H2) products to pass through the membrane 114 to the second or negative electrode side. In 510, gaseous oxygen (O2) can be vented from the first or positive electrode side of hydro core 106, such as through a vent tube or bleed valve.

In 512, hydrogen (H2) gas collected in the second chamber 122 to be communicated as output to a user can be subjected to a coalescer 116, to remove water and/or water vapor from the hydrogen (H2) gas output. In aspects, the coalescer 116 can include a hydrophobic filter or membrane used to divert water and/or water vapor into a catch canister, or other container or channel to be eliminated.

In 514, the hydrogen (H2) gas and/or oxygen (O2) gas can be delivered to a user for consumption. In embodiments, the hydrogen (H2) gas can be delivered via the second port 118 for inhalation by the user, for example using medical grade tubing, breathing mask, and/or a nasal cannula. In embodiments, the hydrogen (H2) and/or oxygen (O2) gas can also or instead be delivered via the second port 118 to be injected or dissolved in water for drinking, for instance using medical grade tubing and an injection nozzle or other mechanism to communicate the hydrogen (H2) gas into water for drinking by the user. In 516, a fault condition such as a threshold temperature (fire), pressure (combustion, acoustic conditions can be detected, and one or more responsive actions, such as cutting power to system 100 and/or shutting down production of hydrogen (H2) gas, can be taken.

In 518, a generation rate of hydrogen (H2) and/or oxygen (O2) gas being produced by the device 100 can be detected via the IOT controller unit 312 and/or other logic, and/or displayed on or via display 314 and/or other output interface or device. In embodiments, various techniques for estimating or determining generation rates and/or flow rates of hydrogen (H2) and/or oxygen (O2) gas, such as by direct volumetric measurements of gas passing through the second port 118 or other points, can be used.

In 520, processing can repeat, return to a prior processing point, jump to a further processing point, or end.

Figure 6:
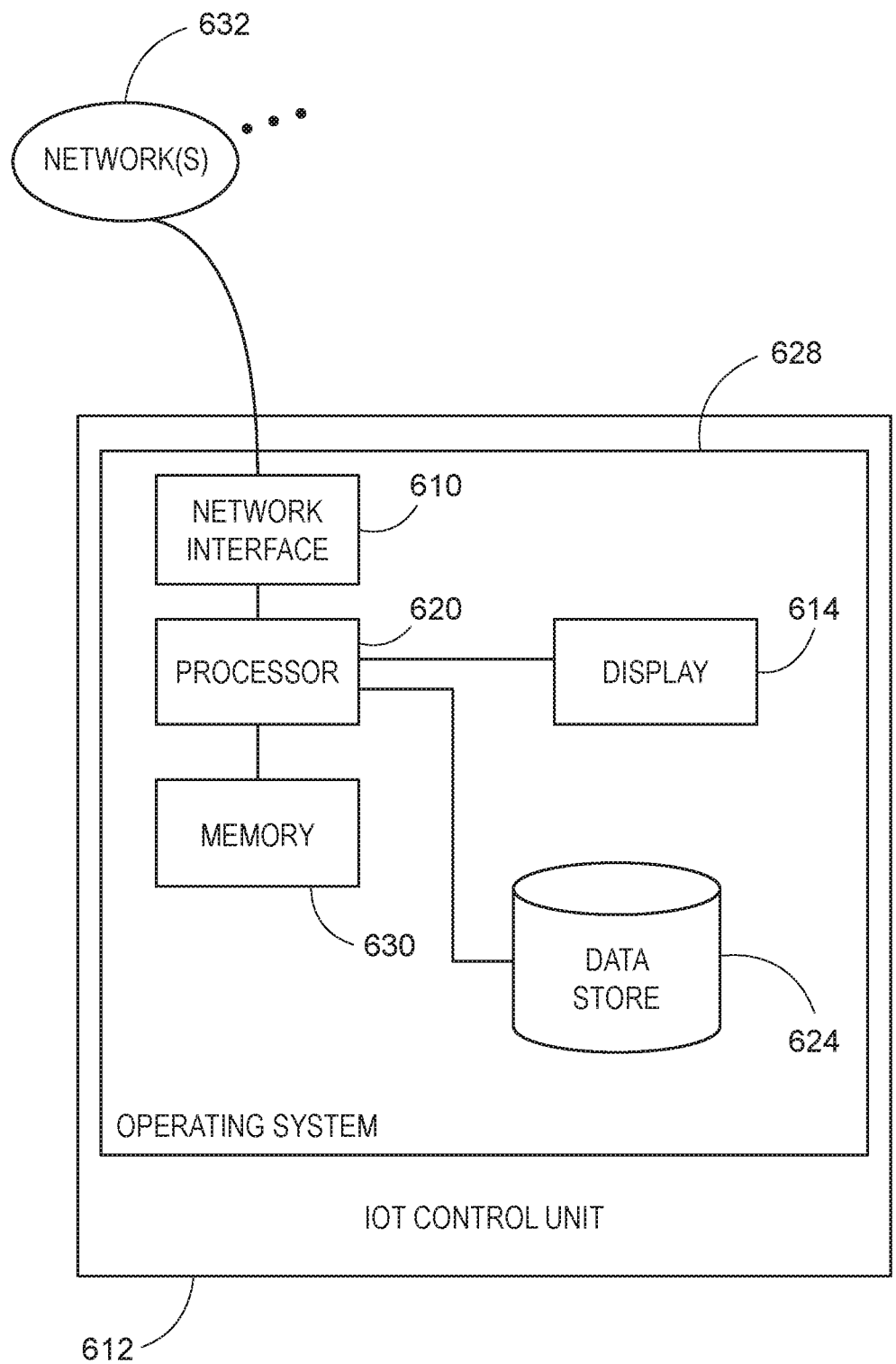
FIG. 6 illustrates exemplary hardware, software, and other resources that can be used in hydrogen gas delivery for personal medical consumption, according to various embodiments.

FIG. 6 illustrates various hardware, software, and other resources that can be used in implementations of hydrogen gas delivery for personal medical consumption, according to embodiments. As shown, an Internet of Things (IOT) control unit 612 can be configured with certain hardware, software, communications and other resources. The IOT control unit 612 can be similar or identical in circuitry and/or function to IOT control unit 312 (e.g. shown in FIG. 3). In embodiments as shown, IOT control unit 612 can comprise a platform including processor 620 communicating with memory 630, such as electronic random access memory, operating under control of or in conjunction with an operating system 628. The processor 620 in embodiments can be incorporated in one or more servers, clusters, and/or other computers or hardware resources, and/or can be implemented using cloud-based resources. The operating system 628 can be, for example, a distribution of the Linux™ operating system, the Unix™ operating system, the Windows™ family of operating systems, and/or other open-source or proprietary operating system or platform. The processor 620 can communicate with the data store 624, such as a database stored on a local or remote hard drive or drive array, to access or store information related to electrical consumption or output, hydrogen (H2) gas and/or other gas generation rates, and/or other information, along with related content, media, or other data. In embodiments, the data store 624 can be configured to store profiles and/or other data for individual users, such as desired generation rates, delivery mechanisms, and/or other information.

The processor 620 can further communicate with a network interface 610, such as an Ethernet or wireless data connection, which in turn communicates with the one or more networks 632, such as the Internet or other public or private networks, which can be or include cloud-based networks or services. In aspects, the processor 620 can also be connected to display 614, to manage and generate the display of hydrogen (H2) gas generation rates, and/or other data to the user via an integrated device or other interface. In aspects, the display 614 can be similar or identical to the display 314 (shown in FIG. 3). In aspects, it will be noted that the power control unit 312 and/or other circuits, modules, logic, and/or controls can be or include resources similar to those of the IOT control unit 312 (FIG. 3), and/or can include additional or different hardware, software, and/or other resources.

Other configurations of the IOT control unit 612 (and 312), power control unit 310, associated network connections, and other hardware, software, and service resources are possible. It will similarly be appreciated that while the IOT control unit 612 (and 312) is described in embodiments as consisting of or including standalone hardware and other resources, in embodiments other computing or communication resources can be used, such as cloud-based networks, storage, and/or services. In embodiments, data captured or stored at the system 100 can be uploaded or transferred to a cloud service for storage or access by the user or others.

The foregoing description is furthermore illustrative, and variations in configuration and implementation may occur to persons skilled in the art. For example, while embodiments have been described in which one reservoir is used to supply water as a working material to system 100 and similar, in embodiments, two or more reservoirs or water supplied or sources can be used. Other resources described as singular or integrated can in embodiments be plural or distributed, and resources described as multiple or distributed can in embodiments be combined. For further example, while examples have been described in applications directed to therapeutic gas delivery, the monitoring, safety, and associated features described herein can be applied to no-medical and/or other applications as desired. The scope of the present teachings is accordingly intended to be limited only by the following claims.

What is claimed is:

1. A device, comprising:
a reservoir;
a first port, connected to the reservoir;
an electrolytic core, connected to the first port to receive water from the reservoir, the electrolytic core comprising:
a first chamber, the first chamber comprising a positive electrode configured to generate oxygen gas in an area of the positive electrode,
a second chamber, the second chamber comprising a negative electrode configured to collect hydrogen gas in an area of the negative electrode, and
a membrane, mounted between the first chamber and the second chamber, the membrane being constructed to communicate the hydrogen gas to the second chamber from the first chamber; and
a second port, connected to the electrolytic core, the second port being configured to communicate at least one of the oxygen or the hydrogen gas at a flow rate useable for continuous consumption by a user via a delivery tube having a set of sensors configured to detect at least one fault condition.

2. The device of claim 1, wherein the set of sensors comprises at least one of:
a pressure sensor,
a temperature sensor,
an optical sensor,
an acoustic sensor, or
an electrical sensor.

3. The device of claim 2, wherein the at least one fault condition comprises at least one of:
an overpressure condition,
an underpressure condition,
an acoustic condition,
a temperature condition, or
a combustion condition.

4. The device of claim 1, wherein the positive electrode comprises at least one of:
a platinum coated electrode, or
a titanium electrode.

5. The device of claim 1, wherein the membrane comprises a PEM membrane.

6. The device of claim 1, further comprising a water coalescer connected to the second port, the water coalescer being configured to remove water or water vapor from the hydrogen gas communicated to the user for consumption.

7. The device of claim 1, further comprising a vent communicating with the first chamber in an area of the positive electrode, the third port being configured to extract water from the area of the positive electrode and communicate the extracted water to the reservoir.

8. The device of claim 3, further comprising a power control unit, the power control unit being configured to control at least one of voltage or current on at least one of the positive electrode or the negative electrode.

9. The device of claim 8, wherein the power control unit is configured to:
monitor the set of sensors, and
initiate a responsive action upon detection of the at least one fault condition.

10. The device of claim 9, wherein the at least one responsive action comprises at least reducing power to the device.

11. The device of claim 8, wherein the voltage is controlled to generate a predetermined oxidation reduction potential of the water outside the electrolytic core.

12. The device of claim 1, wherein the flow rate is adjustable.

13. The device of claim 1, wherein the hydrogen gas is dissolved into water to be dissolved for consumption by the user by drinking.

14. The device of claim 1, wherein at least one of the hydrogen gas or oxygen gas is delivered for inhalation by the user.

15. The device of claim 1, wherein the electrolytic core comprises a set of stackable electrolytic cores.

16. The device of claim 1, further comprising a controller unit configured to monitor a generation rate of the hydrogen gas.

17. The device of claim 1, further comprising a display connected to the controller unit, the display being configured to display at least a generation rate of the hydrogen gas.

18. The device of claim 1, further comprising a network interface configured to connect the device to a network.

19. The device of claim 8, wherein the device is configured to capture information related to the fault condition for transmission to a monitoring service.

* * * * *